(12) United States Patent
Alvarez et al.

(10) Patent No.: US 10,383,765 B2
(45) Date of Patent: Aug. 20, 2019

(54) APPARATUS AND METHOD FOR A GLOBAL COORDINATE SYSTEM FOR USE IN ROBOTIC SURGERY

(71) Applicant: Auris Health, Inc., Redwood City, CA (US)

(72) Inventors: Jeffery B. Alvarez, Redwood City, CA (US); Jian Zhang, Sunnyvale, CA (US); Gregory Kintz, Asheville, NC (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 14/578,082

(22) Filed: Dec. 19, 2014

(65) Prior Publication Data
US 2015/0335480 A1    Nov. 26, 2015

Related U.S. Application Data

(63) Continuation-in-part of application No. 13/868,769, filed on Apr. 23, 2013, now abandoned.
(Continued)

(51) Int. Cl.
*A61B 5/00* (2006.01)
*A61B 3/10* (2006.01)
(Continued)

(52) U.S. Cl.
CPC .......... *A61F 9/00736* (2013.01); *A61B 3/102* (2013.01); *A61B 3/13* (2013.01);
(Continued)

(58) Field of Classification Search
CPC ........ A61F 9/00736; A61B 3/102; A61B 3/13
See application file for complete search history.

(56) References Cited

U.S. PATENT DOCUMENTS

| 4,597,388 A | 7/1986 | Koziol et al. |
| 4,905,673 A | 3/1990 | Pimiskem |

(Continued)

FOREIGN PATENT DOCUMENTS

| EP | 0 830 562 | 7/2009 |
| JP | H09224951 A | 9/1997 |

(Continued)

OTHER PUBLICATIONS

Bourla, Dan H., et al. "Feasibility study of intraocular robotic surgery with the da Vinci surgical system." Retina 28.1 (2008): 154-158.*
(Continued)

*Primary Examiner* — Carolyn A Pehlke
(74) *Attorney, Agent, or Firm* — Knobbe, Martens, Olson & Bear, LLP

(57) ABSTRACT

An apparatus and method for establishing a global coordinate system to facilitate robotic assisted surgery. The coordinate system may be established using a combination of the robotic data, i.e., kinematics, and optical coherence tomographic images generated by an overhead optical assembly and a tool-based sensor. Using these components, the system may generate a computer-registered three-dimensional model of the patient's eye. In some embodiments, the system may also generate a virtual boundary within the coordinate system to prevent inadvertent injury to the patient.

14 Claims, 15 Drawing Sheets

Related U.S. Application Data

(60) Provisional application No. 61/637,426, filed on Apr. 24, 2012.

(51) Int. Cl.
| | | |
|---|---|---|
| *A61B 3/13* | (2006.01) | |
| *A61B 34/30* | (2016.01) | |
| *A61B 90/00* | (2016.01) | |
| *A61F 9/007* | (2006.01) | |

(52) U.S. Cl.
CPC ............ *A61B 5/0059* (2013.01); *A61B 34/30* (2016.02); *A61B 5/0066* (2013.01); *A61B 90/03* (2016.02); *A61B 2090/3735* (2016.02)

(56) References Cited

U.S. PATENT DOCUMENTS

| | | |
|---|---|---|
| 5,402,801 A | 4/1995 | Taylor |
| 5,425,735 A | 6/1995 | Rosen et al. |
| 5,472,406 A | 12/1995 | De La Torre et al. |
| 5,572,999 A | 11/1996 | Funda et al. |
| 5,662,590 A | 9/1997 | De La Torre et al. |
| 5,695,500 A | 12/1997 | Taylor et al. |
| 5,746,720 A | 5/1998 | Stouder |
| 6,033,371 A | 3/2000 | Torre et al. |
| 6,279,579 B1 | 8/2001 | Riaziat |
| 6,326,616 B1 | 12/2001 | Andrien et al. |
| 6,398,792 B1 | 6/2002 | O'Connor |
| 6,406,486 B1 | 6/2002 | De La Tom et al. |
| 6,436,107 B1 | 8/2002 | Wang et al. |
| 6,522,906 B1* | 2/2003 | Salisbury, Jr. ......... A61B 1/313 |
| | | 600/102 |
| 6,554,793 B1 | 4/2003 | Pauker et al. |
| 6,638,246 B1 | 10/2003 | Naimark et al. |
| 6,671,581 B2 | 12/2003 | Niemeyer et al. |
| 6,736,784 B1 | 5/2004 | Menne et al. |
| 6,763,259 B1 | 7/2004 | Hauger et al. |
| 6,850,817 B1 | 2/2005 | Green |
| 7,087,061 B2 | 8/2006 | Chernenko et al. |
| 7,344,528 B1 | 3/2008 | Tu et al. |
| 7,351,193 B2 | 4/2008 | Forman et al. |
| 7,699,855 B2 | 4/2010 | Anderson |
| 7,725,214 B2 | 5/2010 | Diolaiti |
| 7,883,475 B2 | 2/2011 | Dupont et al. |
| 7,967,799 B2 | 6/2011 | Boukhny |
| 8,049,873 B2 | 11/2011 | Hauger et al. |
| 8,224,484 B2 | 7/2012 | Swarup et al. |
| 8,414,564 B2 | 4/2013 | Goldshleger et al. |
| 8,469,947 B2 | 6/2013 | Devengenzo |
| 8,506,555 B2 | 8/2013 | Ruiz Morales |
| 8,518,024 B2 | 8/2013 | Williams et al. |
| 8,827,948 B2 | 9/2014 | Romo et al. |
| 9,173,713 B2 | 11/2015 | Hart et al. |
| 9,226,796 B2 | 1/2016 | Bowling |
| 9,254,123 B2 | 2/2016 | Alvarez et al. |
| 9,480,534 B2 | 11/2016 | Bowling |
| 9,504,604 B2 | 11/2016 | Alvarez |
| 9,561,083 B2 | 2/2017 | Yu et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,795,445 B2 | 10/2017 | Bowling |
| 9,820,818 B2 | 11/2017 | Malackowski |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,681 B2 | 3/2018 | Wallace et al. |
| 10,004,562 B2 | 6/2018 | Kostrzewski |
| 10,004,569 B2 | 6/2018 | Singh |
| 10,016,900 B1 | 7/2018 | Meyer et al. |
| 10,022,192 B1 | 7/2018 | Ummalaneni |
| 2002/0193685 A1 | 12/2002 | Mate |
| 2004/0030349 A1 | 2/2004 | Boukhny |
| 2004/0135733 A1 | 7/2004 | Chou et al. |
| 2005/0070844 A1 | 3/2005 | Chow et al. |
| 2006/0079756 A1 | 4/2006 | Lloyd et al. |
| 2007/0032906 A1 | 2/2007 | Sutherland et al. |
| 2007/0135763 A1 | 6/2007 | Musbach et al. |
| 2007/0144298 A1* | 6/2007 | Miller ................... B25J 9/1676 |
| | | 74/490.01 |
| 2007/0270685 A1* | 11/2007 | Kang .................. A61B 17/1764 |
| | | 600/424 |
| 2007/0299427 A1 | 12/2007 | Yeung et al. |
| 2008/0065109 A1 | 3/2008 | Larkin |
| 2008/0097293 A1 | 4/2008 | Chin et al. |
| 2008/0114341 A1 | 5/2008 | Thyzel |
| 2008/0177285 A1 | 7/2008 | Brock et al. |
| 2008/0187101 A1 | 8/2008 | Gertner |
| 2008/0228104 A1 | 9/2008 | Uber et al. |
| 2009/0062602 A1 | 3/2009 | Rosenberg et al. |
| 2009/0088634 A1* | 4/2009 | Zhao ..................... B25J 9/1689 |
| | | 600/427 |
| 2009/0099445 A1* | 4/2009 | Burger .................. A61B 90/36 |
| | | 600/424 |
| 2009/0171271 A1 | 7/2009 | Webster et al. |
| 2009/0248037 A1 | 10/2009 | Prisco |
| 2009/0248038 A1* | 10/2009 | Blumenkranz ........ B25J 13/085 |
| | | 606/130 |
| 2009/0248041 A1 | 10/2009 | Williams et al. |
| 2009/0248043 A1 | 10/2009 | Tierney et al. |
| 2009/0264878 A1 | 10/2009 | Carmel et al. |
| 2009/0268015 A1 | 10/2009 | Scott et al. |
| 2009/0312768 A1 | 12/2009 | Hawkins et al. |
| 2009/0326322 A1 | 12/2009 | Diolaiti |
| 2010/0036294 A1 | 2/2010 | Mantell et al. |
| 2010/0073150 A1 | 3/2010 | Olson et al. |
| 2010/0228191 A1 | 9/2010 | Alvarez et al. |
| 2010/0234999 A1 | 9/2010 | Nakajima |
| 2010/0280320 A1 | 11/2010 | Alvarez et al. |
| 2010/0280525 A1 | 11/2010 | Alvarez et al. |
| 2011/0009779 A1 | 1/2011 | Romano et al. |
| 2011/0015648 A1 | 1/2011 | Alvarez et al. |
| 2011/0152880 A1 | 1/2011 | Alvarez et al. |
| 2011/0028887 A1 | 2/2011 | Fischer et al. |
| 2011/0040404 A1 | 2/2011 | Diolaiti et al. |
| 2011/0046441 A1 | 2/2011 | Wiltshire et al. |
| 2011/0106102 A1 | 5/2011 | Balicki et al. |
| 2011/0144479 A1 | 6/2011 | Hastings et al. |
| 2011/0306836 A1 | 12/2011 | Ohline et al. |
| 2012/0046542 A1 | 2/2012 | Csavoy et al. |
| 2012/0138586 A1 | 6/2012 | Webster et al. |
| 2012/0283747 A1 | 11/2012 | Popovic |
| 2013/0041509 A1 | 2/2013 | Saito |
| 2013/0072787 A1 | 3/2013 | Wallace et al. |
| 2013/0144116 A1 | 6/2013 | Cooper et al. |
| 2013/0274596 A1* | 10/2013 | Azizian ................ A61B 5/0071 |
| | | 600/424 |
| 2014/0012276 A1 | 1/2014 | Alvarez |
| 2014/0052154 A1 | 2/2014 | Griffiths |
| 2014/0094968 A1* | 4/2014 | Taylor .................... B25J 13/006 |
| | | 700/257 |
| 2014/0142591 A1 | 5/2014 | Alvarez et al. |
| 2014/0276594 A1 | 9/2014 | Tanner et al. |
| 2014/0276933 A1 | 9/2014 | Hart et al. |
| 2014/0309649 A1 | 10/2014 | Alvarez et al. |
| 2014/0357984 A1 | 12/2014 | Wallace et al. |
| 2014/0364870 A1 | 12/2014 | Alvarez et al. |
| 2014/0379000 A1 | 12/2014 | Romo et al. |
| 2015/0025539 A1 | 1/2015 | Alvarez et al. |
| 2015/0051592 A1 | 2/2015 | Kintz |
| 2015/0101442 A1 | 4/2015 | Romo |
| 2015/0119637 A1 | 4/2015 | Alvarez et al. |
| 2015/0119638 A1 | 4/2015 | Yu et al. |
| 2015/0164594 A1 | 6/2015 | Romo et al. |
| 2015/0164595 A1 | 6/2015 | Bogusky et al. |
| 2015/0164596 A1 | 6/2015 | Romo et al. |
| 2015/0248121 A1 | 9/2015 | Nilsson |
| 2015/0374446 A1 | 12/2015 | Malackowski |

(56) References Cited

U.S. PATENT DOCUMENTS

| | | |
|---|---|---|
| 2016/0001038 A1 | 1/2016 | Romo et al. |
| 2016/0100896 A1 | 4/2016 | Yu |
| 2016/0144509 A1 | 5/2016 | Gulhar |
| 2016/0151122 A1 | 6/2016 | Alvarez et al. |
| 2016/0022189 A1 | 8/2016 | Nilsson et al. |
| 2016/0221189 A1 | 8/2016 | Nilsson |
| 2016/0270865 A1 | 9/2016 | Landey et al. |
| 2016/0279405 A1 | 9/2016 | Riley |
| 2016/0287279 A1 | 10/2016 | Bovay et al. |
| 2016/0296294 A1 | 10/2016 | Moll et al. |
| 2016/0354925 A1 | 12/2016 | Shimodaira |
| 2016/0374541 A1 | 12/2016 | Agrawal et al. |
| 2017/0007336 A1 | 1/2017 | Tsuboi |
| 2017/0007337 A1 | 1/2017 | Dan |
| 2017/0007342 A1 | 1/2017 | Kasai |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0165834 A1 | 6/2017 | Hares |
| 2017/0172673 A1 | 6/2017 | Yu et al. |
| 2017/0172680 A1 | 6/2017 | Bowling |
| 2017/0202627 A1 | 7/2017 | Sramek et al. |
| 2017/0209073 A1 | 7/2017 | Sramek et al. |
| 2017/0245955 A1 | 8/2017 | Bowling |
| 2017/0274530 A1 | 9/2017 | Mottram |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055583 A1 | 3/2018 | Schuh et al. |
| 2018/0177383 A1 | 6/2018 | Noonan et al. |
| 2018/0177556 A1 | 6/2018 | Noonan et al. |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |

FOREIGN PATENT DOCUMENTS

| | | |
|---|---|---|
| WO | WO 92/14411 A1 | 9/1992 |
| WO | WO 03/096871 A2 | 11/2003 |
| WO | WO 2004/105849 A1 | 12/2004 |
| WO | WO 2011/161218 A1 | 12/2011 |

OTHER PUBLICATIONS

Skarecky, Douglas W., Matthew Brenner, Sudhir S. Rajan, Esequiel Rodriguez, Navneet Narula, Frank Melgoza, and Thomas E. Ahlering. "Zero positive surgical margins after radical prostatectomy: is the end in sight?." Expert review of medical devices 5, No. 6 (2008): 709-717.*
European search report and search opinion dated Jul. 2, 2015 for EP Application No. 12856685.8.
Office action dated May 21, 2015 for U.S. Appl. No. 13/711,440.
Office action dated Jun. 11, 2015 for U.S. Appl. No. 14/158,548.
U.S. Appl. No. 14/201,610, filed Mar. 7, 2014, Romo.
U.S. Appl. No. 14/458,042, filed Aug. 12, 2014, Kintz.
U.S. Appl. No. 14/523,760, filed Oct. 24, 2014, Alvarez et al.
U.S. Appl. No. 14/542,373, filed Nov. 14, 2014, Romo et al.
U.S. Appl. No. 14/542,387, filed Nov. 14, 2014, Bogusky et al.
U.S. Appl. No. 15/542,403, filed Nov. 14, 2014, Yu et al.
U.S. Appl. No. 14/542,429, filed Nov. 14, 2014, Romo et al.
U.S. Appl. No. 14/583,021, filed Dec. 24, 2014, Romo et al.
U.S. Appl. No. 62/037,520, filed Aug. 14, 2014, Yu.
Balicki, et al. Single fiber optical coherence tomography microsurgical instruments for computer and robot-assisted retinal surgery. Medical Image Computing and Computer-Assisted Intervention. MICCAI 2009. Springer Berlin Heidelberg, 2009. 108-115.
Ehlers, et al. Integration of a spectral domain optical coherence tomography system into a surgical microscope for intraoperative imaging. Investigative Ophthalmology and Visual Science 52.6. 2011; 3153-3159.
Hubschman. Robotic Eye Surgery: Past, Present, and Future. Journal of Computer Science and Systems Biology. 2012.
International search report and written opinion dated Jan. 27, 2015 for PCT Application No. US2014/062284.
International search report and written opinion dated Mar. 29, 2013 for PCT/US2012/069540.
International search report and written opinion dated Nov. 7, 2014 for PCT Application No. US2014/041990.
International search report dated Jun. 16, 2014 for PCT/US2014/022424.
Office action dated Oct. 7, 2014 for U.S. Appl. No. 13/711,440.
Office action dated Jun. 19, 2014 for U.S. Appl. No. 13/868,769.
Stoyanov. Surgical vision. Annals of Biomedical Engineering 40.2. 2012; 332-345. Published Oct. 20, 2011.
Verdaasdonk, et al. Effect of microsecond pulse length and tip shape on explosive bubble formation of 2.78 iLtm Er,Cr;YSGG and 2.94 iLtm Er:YAG laser. Paper 8221-12, Proceedings of SPIE, vol. 8221 (Monday Jan. 23, 2013).

* cited by examiner

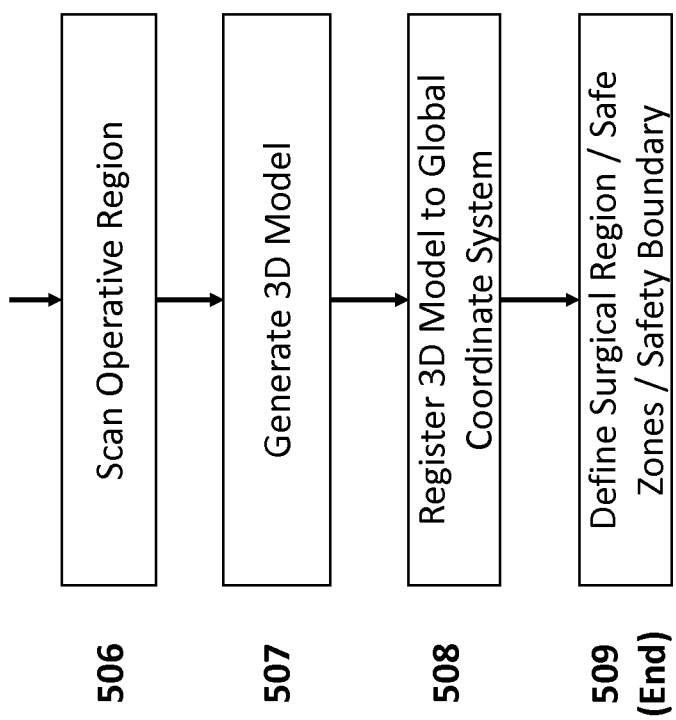

APPARATUS AND METHOD FOR A GLOBAL COORDINATE SYSTEM FOR USE IN ROBOTIC SURGERY

CROSS-REFERENCE TO RELATED APPLICATIONS

This application is a continuation-in-part of U.S. patent application Ser. No. 13/868,769, filed Apr. 23, 2013, which claims priority from U.S. Provisional Application No. 61/637,426, filed Apr. 24, 2012, the entire contents of which are incorporated by reference.

BACKGROUND OF THE INVENTION

1. Field of the Invention

The field of the present application pertains to medical devices. More particularly, the field of the invention pertains to an apparatus and method for a global coordinate system for use in robotic-assisted surgery.

Embodiments described herein are directed to a new method, apparatus, and system for generating and operating a global coordinate system that may be useful for performing robotically-assisted surgery.

2. Description of the Related Art

Present microsurgical procedures are currently extremely technique dependent. For example, several existing solutions for eye surgery involve various techniques with lasers and phacoemulsification.

Modern extracapsular cataract surgery is usually performed using a microsurgical technique called phacoemulsification, whereby the cataract is emulsified with an ultrasonic hand piece and then suctioned out of the eye. Before phacoemulsification can be performed, one or more incisions are made in the eye to allow the introduction of surgical instruments. The surgeon then removes the anterior face of the capsule that contains the lens inside the eye. A phacoemulsification probe is an ultrasonic hand piece with a titanium or steel needle. The tip of the needle vibrates at ultrasonic frequency to sculpt and emulsify the cataract while a pump aspirates particles through the tip. In some techniques, a second fine steel instrument called a chopper is used from a side port to help with chopping the nucleus into smaller pieces. The cataract is usually broken into numerous pieces and each piece is emulsified and aspirated out with suction. The nucleus emulsification makes it easier to aspirate the particles. After removing all hard central lens nucleus with phacoemulsification, the softer outer lens cortex is removed with suction only. As with other cataract extraction procedures, an intraocular lens implant (IOL), is placed into the remaining lens capsule.

One possible improvement to phacoemulsification is a cataract surgery performed with lasers. Femtosecond laser cataract surgery is rapidly emerging as a potential technology that may allow for improved precision of incision formation and emulsification of the cataract. Although phacoemulsification and laser-based cataract surgery work well for many patients, these technologies have several shortcomings. For example, phacoemulsification ultrasound probes must propagate ultrasound energy along the length of the probe, from a proximal transducer to a distal tip. This propagation may lead to transmission of ultrasound energy along the probe to tissues in and around the eye that do not benefit from the transmission. Current lens emulsifying probes generate cavitation energy that is initiated within the area of lens nucleus and radiates outwards towards the lens capsule. This places the lens capsule at risk for damage by this energy. Ultrasound probes also tend to generate more heat than would be desirable for a procedure in the eye.

Finally, it may be quite difficult to steer an ultrasound probe around corners or bends, due to the mechanical requirements of propagating the ultrasound wave along the entire instrument. In other words, the probe may have to be rigid or at least more rigid than would be desirable.

Probe based lasers have similar drawbacks. They may generate unwanted heat in the eye and are often difficult to control, thus risking damage to important nearby tissues. They also are easily damaged when attempting to navigate tight corners, as fibers in a laser probe may easily break.

Femtosecond laser systems have been devised to assist in the removal of cataracts. These devices are used to create the entry sites through the cornea and sclera into the eye, as well as to remove the anterior face of the capsule. In addition, the femtosecond laser energy can be focused within the lens nucleus itself, and used to "pre-chop" the lens nucleus into a number of pieces that can then be more easily removed with the phacoemulsification probe. However, these lasers can only fragment the center zone of the lens that is visible within the pupil (the iris blocks the peripheral lens from laser energy), so that fracture and removal of the peripheral lens by another method is still necessary. They are costly to own and operate and have the additional drawback of extending operative time.

The aforementioned techniques require extreme precision for successfully completion and minimal complications. Therefore, it would be beneficial to have an apparatus and method for a global coordinate system for assisting performing surgery for various applications including eye, microsurgery, and/or other emulsification applications.

SUMMARY OF THE INVENTION

In general, the present invention provides for a global coordinate system for use in robotically-assisted surgery. In one aspect, the present invention provides for a system for facilitating robotic surgery comprising a first mechanical arm configured to facilitate operation of an optical assembly that comprises a first optical coherence tomographical imaging system; a second mechanical arm operatively coupled to operate a surgical tool, the surgical tool comprising a second optical coherence tomographical imaging system, and a coordinate system processing unit configured to generate a global coordinate system using optical coherence tomographic data generated by the first optical coherence tomographical imaging system and the second optical coherence tomographical imaging system, and kinematic registration data based on the location of the first mechanical arm, second mechanical arm, and the tool.

In related systems, the first mechanical arm is robotically-driven. In some systems, the second mechanical arm is robotically-driven. In some systems, the coordinate system processing unit is further configured to define a virtual boundary for avoiding inadvertent injury to patient tissue and anatomy. In some systems, the virtual boundary restricts movement of the second mechanical arm. In some systems, movement of the second mechanical arm into the virtual boundary triggers auditory feedback. In some systems, the second optical coherence tomographical system is configured to generate images of tissue topology.

In related systems, the optical assembly further comprises a visual light microscope configured for positioning the optical assembly over the eye of a patient. In some systems, the optical assembly further comprises a shared lens stack configured to be used by both the visual light microscope and the first optical coherence tomographical system.

In another aspect, the present invention provides a method for facilitating robotic surgery using a global coordinate system comprising registering the location of an optical assembly with a predetermined focal length that is operatively coupled to the flange of a mechanical arm, orienting the optical assembly over a patient's eye, registering the location of the patient's eye using the predetermined focal length of the optical assembly, scanning the patient's eye using an optical tomographical system integrated into the optical assembly, retrieving optical tomographical data, processing the data to generate a three-dimensional model of the patient's eye, and integrating the three-dimensional model into a global coordinate system that has been registered to the location of the mechanical arm.

BRIEF DESCRIPTION OF THE DRAWINGS

These and other aspects and embodiments will be described in greater detail below, in reference to the attached drawing figures.

FIGS. 5A and 5B illustrate a flow diagram that details the steps for initializing system 400 after the patient has been positioned on the operating table;

DETAILED DESCRIPTION OF THE INVENTION

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

A. Surgical Robotic Arm Platform.

Figure 1:
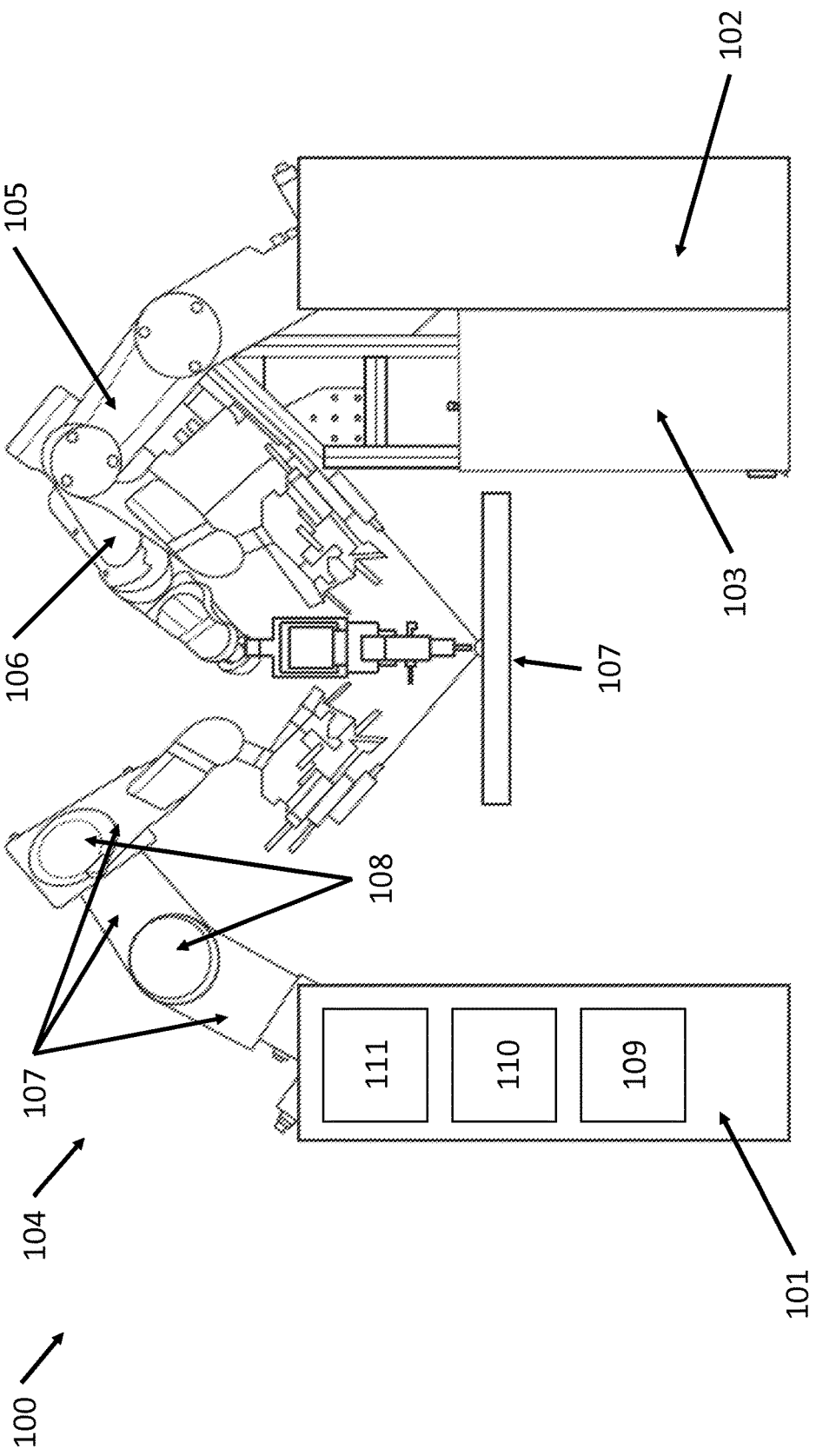
FIG. 1 illustrates a robotic surgical system, in accordance with an embodiment of the present invention.

FIG. 1 illustrates a robotic surgical system, in accordance with an embodiment of the present invention. Robotic system 100 may comprise several system carts 101, 102, and 103 with at least one mechanical arm, such as arms 104, 105, and 106 respectively. The system carts may be in communication with a remotely-located command console (not shown). In practice, the system carts may be arranged to provide access to a patient located on workspace 107, while a physician may control the system 100 from the comfort of the command console. In some embodiments, the system cart may be integrated into the operating table or bed for stability and access to the patient. Alternatively, robotic system 100 may be tethered to a single cart.

Mechanical arm 104 may be fixedly coupled to system cart 101 which contains a variety of support systems, including control electronics, power sources and optical sources in some embodiments. The arm 104 may be formed from a plurality of linkages 107 and joints 108 to enable access to the patient. The system cart 101 may contain a source of power 109, pneumatic pressure 110, and control and sensor electronics 111—including components such as central processing unit, data bus, control circuitry, and memory—and related actuators or motors that may drive arms such as arm 104. Power may be conveyed from the system cart 101 to the arm 104 using a variety of means known to one skilled in the art such as electrical wiring, gear heads, air chambers. The electronics 111 in system cart 101 may also process and transmit control signals communicated from a command console. System carts 102 and 103 and arms 105 and 106 may be similarly configured to system cart 101 and arm 104.

The system cart 101 may also be mobile. In some embodiments, the system cart may capable of being wheeled to the desired location near the patient. System carts 101, 102, and 103 may be located in various locations in the operating room in order to accommodate space needs and facilitate appropriate placement and motion of modules and instruments with respect to a patient. This capability enables the arms to be positioned in locations where they do not interfere with the patient, doctor, anesthesiologist or any supportive surgical equipment required for the selected procedure. During procedures, the arms with instruments will work collaboratively via user control through separate control devices, which may include a command console with haptic devices, joystick, or customized pendants.

If mechanical arm 104 is robotic, joints 108 may comprise one or more actuators in order to affect movement in at least one degree of freedom. The arm 104, as a whole, preferably has more than three degrees of freedom. Through a combination of wires and circuits, each arm may also convey both power and control signals from system cart 101 to the instruments located at the end of their extremities.

In some embodiments, the arms may be fixedly coupled to the operating table with the patient. In some embodiments, the arms may be coupled to the base of the operating table and reach around to access patient.

In some embodiments, the arms may be capable of external "force drag" in order to affect precise positioning. Force drag, a type of cooperative force control, allows an operator to manually adjust and move an arm to a desired position and location. In the right situation, cooperative force control provides extremely precise, tremor-free motion while preserving much of the transparency and naturalness of conventional manual instrument manipulation.

Figure 2:
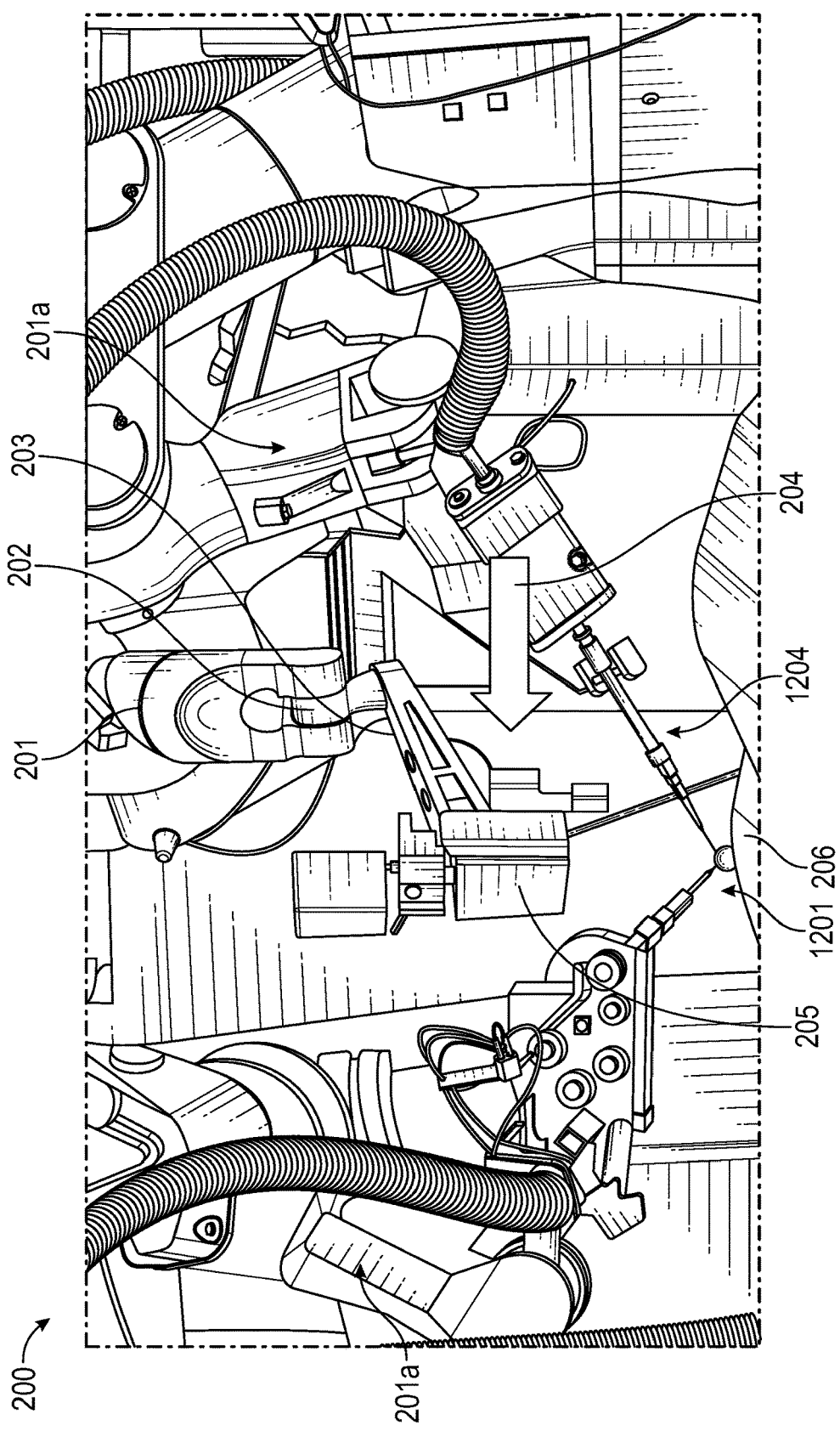
FIG. 2 illustrates force drag through the use of a force-torque sensor in a flange joint, in accordance with an embodiment of the present invention.

FIG. 2 illustrates force drag through the use of a force-torque sensor in a flange joint, in accordance with an embodiment of the present invention. As shown in FIG. 2, system 200 may include an arm 201 with a force-torque sensor located at the flange joint 202 between the arm 201 and end effector 203. In robotics parlance, a flange joint is external to the robotic system, e.g., the arms in this particular embodiment. The force-torque sensor in joint 202 may detect and measure external operator interaction force 204 in an effort to move an attached OCT scanner and camera 205 over an operative site 206. A six-degree force-torque sensor may measure force in three directions (x, y, and z axes) and three torque in three directions (x, y, and z axes). In response, the system 200 may respond by making precise, tremor-free motions to comply with the operator's commands. The system 200 may include a plurality of robotic arms, such as a second arm 201a and a third arm 201b. One or more of the second arm 201a or the third arm 201b may be similar to first arm 201. The second robotic arm 201a may be operatively coupled to a first surgical tool 1201 (further described below) so that the second robotic arm 201a may be used to insert the first surgical tool 1201 into an eye. The third robotic arm 201b may be operatively coupled to a second surgical tool 1204 (further described below) for insertion into the eye as well. The first robotic tool 1201 and the second robotic tool 1204 may be similar to the surgical tool 1002 and may be configured with an OCT fiber and coupled to an OCT scanner and detector as described below.

Figure 3:
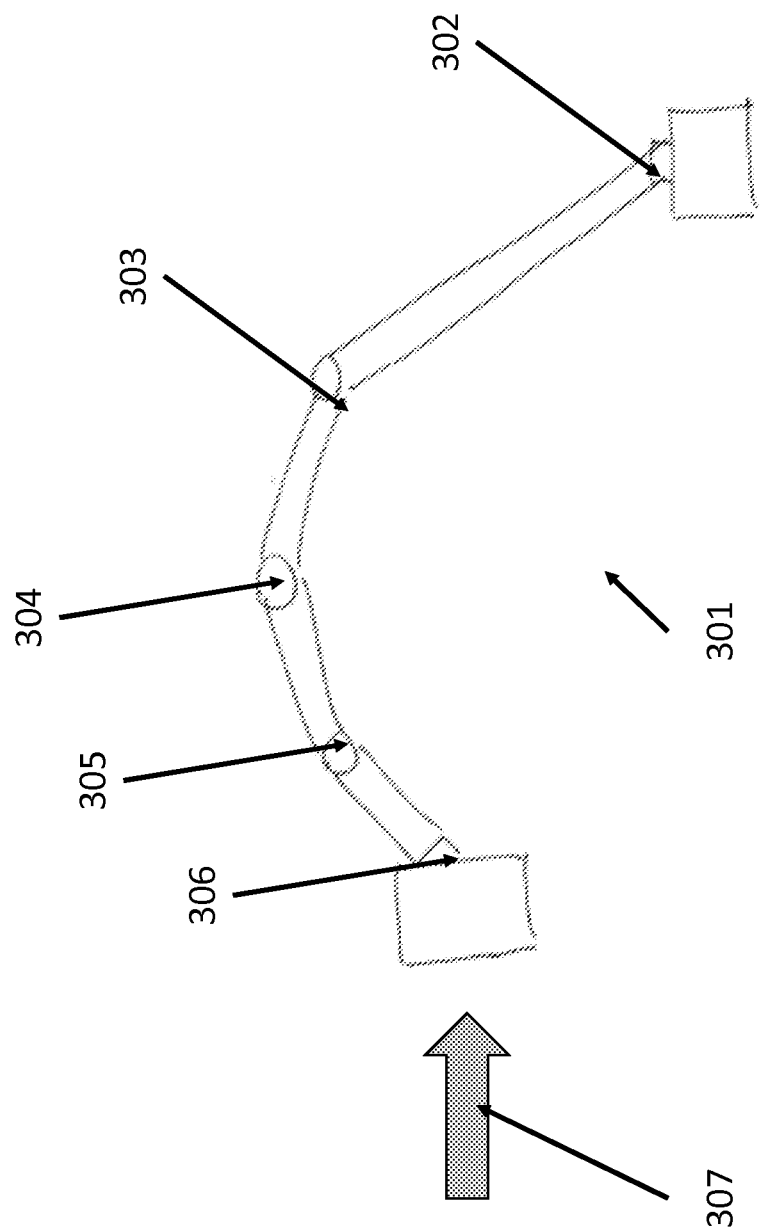
FIG. 3 illustrates force drag in a system that does not use force sensors, in accordance with an embodiment of the invention.

In some embodiments, the force drag capability may be implemented without a complicated force-torque sensor. FIG. 3 illustrates force drag in a system that does not use force sensors, in accordance with an embodiment of the invention. In system 300, a robotic arm 301 with 5 joints (302, 303, 304, 305, and 306) may be constructed with 5 integrated torque sensors, one torque sensor per joint. While only able to detect one degree of torque per joint, sampling all the sensors in response to an external force 307 allows system 300 to generate a corresponding matrix of the motion felt across the entire arm 301. The resulting matrix may be applied to the Jacobian of the arm 301, allowing for system 300 to calculate the external force 307. Using that information, system 300 may be able to respond like system 200 from FIG. 2, and make precise, tremor-free motions that comply with the operator's force.

In one embodiment, the system provides six degrees of freedom (DOF) for a given end effector. Three DOFs may be accounted in the Cartesian x-, y-, z- axes by moving the arm 104 from FIG. 1 independent of the end effector. The remaining three DOFs (pitch, yaw, and roll) of the end effector may be achieved by manipulation through a pivot point. The high number of DOFs allows the end effector to be carefully positioned in close proximity to the operative site, such as the cornea of a patient.

In one embodiment, the end effector includes an instrument drive mechanism that has additional DOF control in the form of both mechanical insertion/retraction and roll, and pneumatic insertion/retraction. An instrument drive mechanism with DOF control allows for instrument motion to be localized to the distal end of the system, and reduces the amount of motion required of the arm.

B. Global Coordinate System Using Optical Coherence Tomography.

In conjunction with a robotic surgical platform, the present invention provides for a global coordinate system to map the three-dimensional space both outside and inside the operative region in the patient. In the context of ophthalmology, the three dimensional mapping of the operative region, i.e., the eye, may be accomplished through a combination of visual optics and optical coherence tomographical (OCT) scanning.

Figure 4:
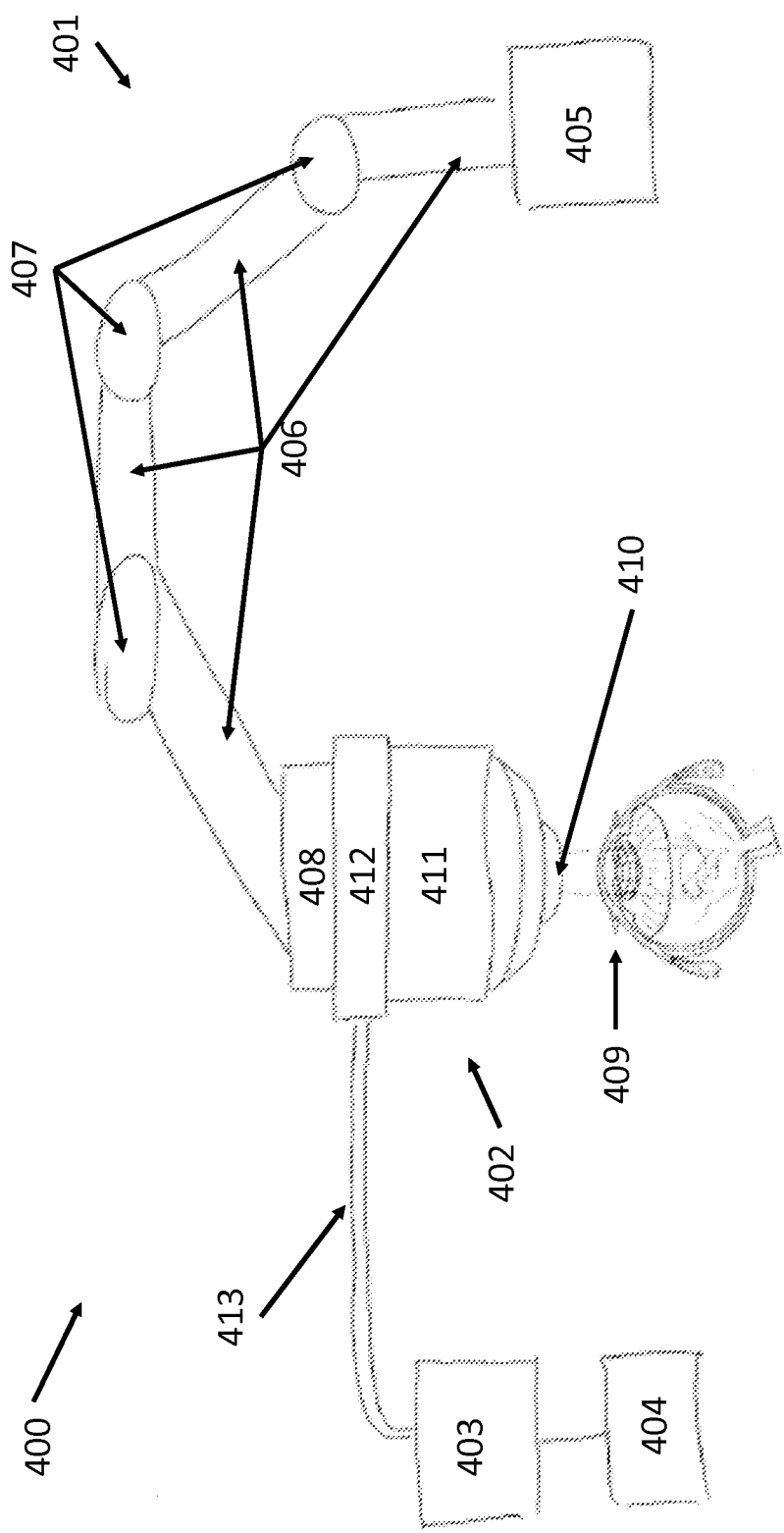
FIG. 4 is a perspective view of an apparatus for a GOCT (Global Optical Coherence Tomography) system, according to one embodiment of the present invention.

FIG. 4 is a perspective view of an apparatus for a global coordinate system, according to an embodiment of the present invention. System 400 principally comprises a mechanical arm 401, an optical assembly 402, a laser emitter/detector 403, and a processing unit 404. The proximal end of arm 401 may be fixedly mounted or coupled to the system base 405. Mechanical arm 401 comprises a plurality of linkages 406 connected by at least one joint per arm, such as joints 407. If mechanical arm 401 is robotic, joints 407 may comprise one or more actuators in order to affect movement in at least one degree of freedom. In some embodiments, the joints may also comprise of a force or torque sensor. Through a combination of wires and circuits, arm 401 may also convey both power and control signals from system base 405 to the flange joint 408 to optical assembly 402 if needed.

As in other embodiments, system base 405 may contain a variety of support systems, including control electronics, power sources and optical sources in some embodiments. The system base 405 may contain source of power, pneumatic pressure, and control and sensor electronics—including components such as central processing unit, data bus, control circuitry, and memory—and related actuators or motors that may drive arms such as arm 401. Power may be conveyed from the system base 405 to the arm 401 using a variety of means known to one skilled in the art such as electrical wiring, gear heads, air chambers. The electronics in system base 405 may also process and transmit control signals communicated from a remotely-located command console. In some embodiments, the system base 405 may be coupled or integrated with the laser unit 403 and processing unit 404.

As in other embodiments, the system base 405 may also be mobile. In some embodiments, the system base 405 may be located in various locations in the operating room in order to accommodate space needs and facilitate appropriate placement and motion of modules and instruments with respect to a patient. As in other embodiments, arm 401 may be fixedly coupled to the operating table with the patient. In some embodiments, arm 401 may be coupled to the base of the operating table and reach around to access patient.

Arm 401 may position optical assembly 402 over an operative site such as eye 409. In some embodiments, arm 401 may be referred to as a "vision arm" due to its use with optical assembly 402. In some embodiments, arm 401 may be configured to enable six degrees of freedom control of optical assembly 402 or stereo-optic video system to provide an ideal clinical perspective for the operator.

Optical assembly 402 may comprise of a lens 410, a lens stack 411, minor reflecting unit 412. Optical assembly 402 works in conjunction with laser emitter/detector unit 403, laser fiber 413. As is understood in the art, an optical coherence tomography (OCT) system operates by emitting laser energy of a predetermined wavelength over an operative region and measuring the scattering of the laser energy that results from interaction with tissue and human anatomy. Scattering often occurs when the index of refraction changes, typically at the interface between different tissues.

Within system 400, the laser energy may be generated by laser unit 403 and conveyed to the optical assembly 402 through the laser fiber 413. In some embodiments, laser unit 403 may be capable of emitting laser light of fixed wavelengths varying from 860 nm to 1300 nm, including wavelengths of 860 nm, 1030 nm, 1040 nm, and 1300 nm. Using shorter wavelengths allows for higher axial resolutions in the OCT image, while sacrificing tissue depth penetration. Conversely, using longer wavelengths generally results in lower axial resolution in the OCT image but provides for greater tissue depth penetration.

Laser fiber 413 may be sheathed by any conventional means such as wiring, castings, or coating. Having reached the optical assembly 402, the laser energy may be redirected through the lens stack 411 by the reflecting unit 412. Reflecting unit 412 may comprise minors and reflectors that are manipulated by a galvanometer to direct laser energy through the lens stack 411 and lens 410 into particular regions of the operative site 409. The galvanometer within reflecting unit 412 may direct the laser energy in a precise pattern to scatter laser energy in a measurable pattern.

Depending on the tissues encountered by the laser energy emerging from lens 410, the laser energy may be absorbed, reflected and refracted, scattering the laser energy. The reflected scattered laser energy may be captured through the lens 410 and lens stack 411, reflected back to the laser fiber 413 by the reflecting unit 412, and detected by laser unit 403. Based on the strength and scattering of the reflected laser energy, system 400 may be able to visualize tissue contours and depth in the operative site in three dimensions.

Figure 5A:
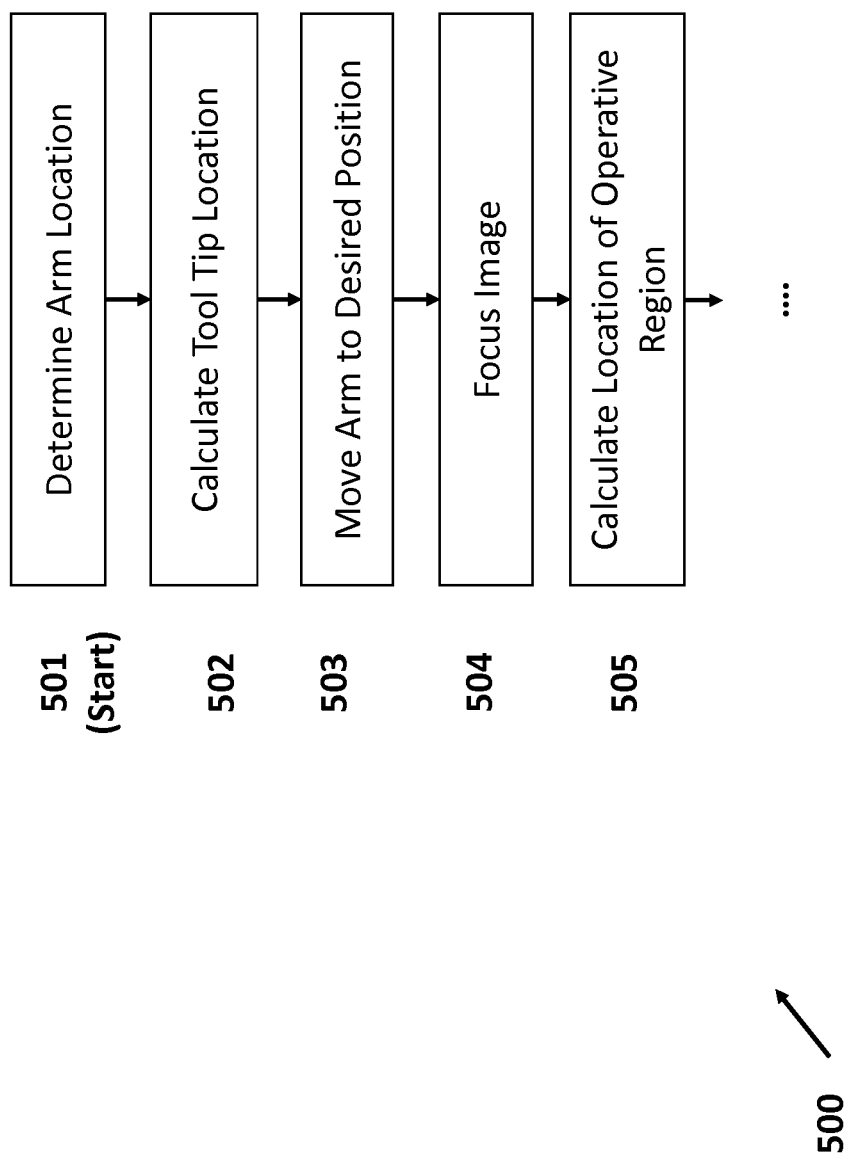

FIG. 5 illustrates a flow diagram that details the steps for initializing system 400 after the patient has been positioned on the operating table. To start process 500, in step 501, the system 400 may first register the arm 401 to the system base 405. Specifically, step 501 involves determining the location of the linkages 406 of the arm 401, based on sensors in the joints 407. In some embodiments, this may involve receiving information from the sensors in the joints 407, such as torque sensors. Based on the readings from sensors mounted in joints 407, and the known sizes of the linkages 407, the system 400 may calculate the arm locations using Jacobian and kinematics calculations. As the joint sensors may continually transmit readings back to the system base 405, arm location may be continually updated and verified to ensure that the location is accurate in real-time use.

In step 502, the system 400 registers the location of the tool tip, i.e., the location of lens 410 at the tip of the optical assembly 402. This location may be derived from the location of the tip of the robot arm (flange joint 408) and the size of the optical assembly 402. Thus, in combination with arm registration performed in step 501, the system 400 may be able to register the optical assembly to the system base 405, which acts as an anchor in the global coordinate system.

In step 503, the operator may manually move the arm 401 and optical assembly 402 to a desired position over the patient's operative site, i.e., eye. The desired position generally provides a clear line of sight between the optical assembly and the operative site in order for the OCT system to properly scan the site. In some embodiments, the optical assembly is positioned in an overhead position above the patient in order to access the operative site. The optical assembly 402 includes means of aiming and positioning the optical assembly over the site. In some embodiments, this may involve using a camera that makes use of the same lens stack as the OCT system.

Figure 6:
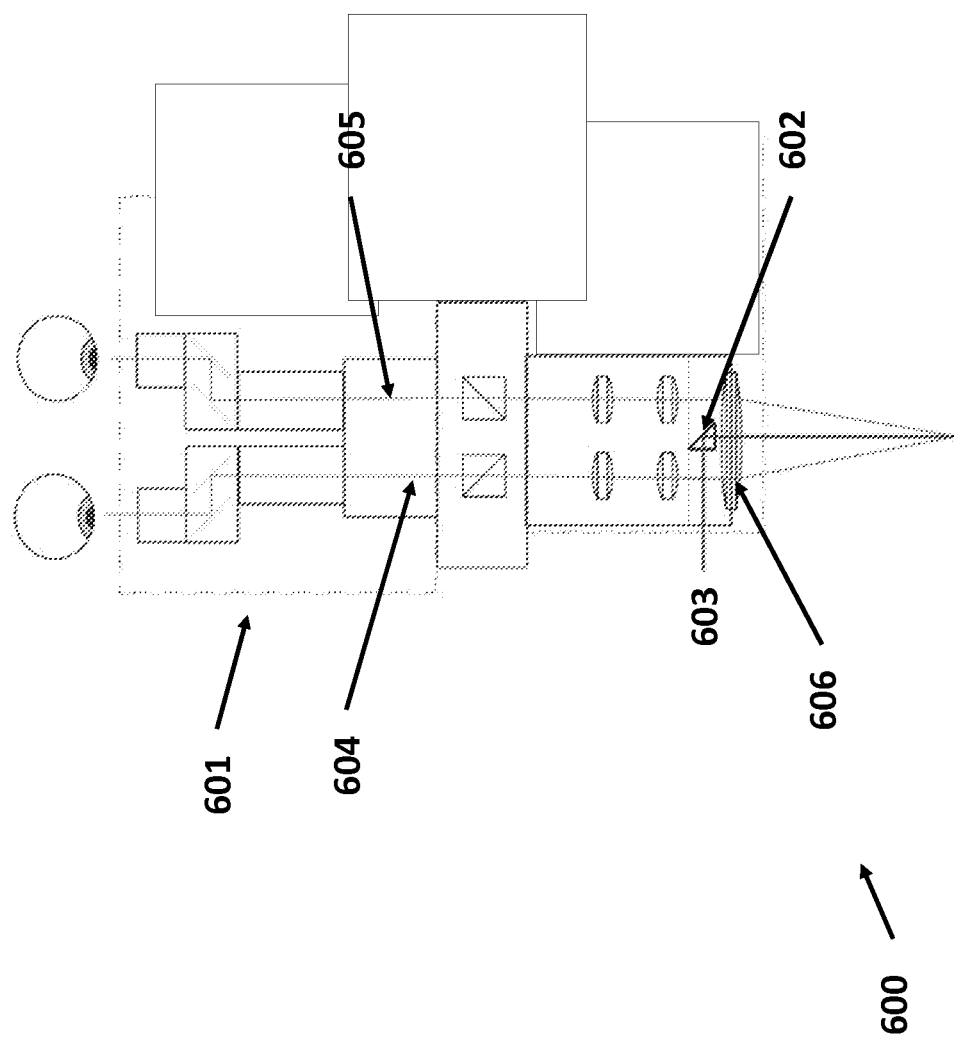
FIG. 6 illustrates an optical apparatus that uses shared optics for both a visual light microscope and an OCT system, in accordance with an embodiment of the present invention.

FIG. 6 illustrates an optical apparatus that uses shared optics for both a visual light microscope and an OCT system, in accordance with an embodiment of the present invention. As shown in system 600, which may be attached at the flange of a robotic arm, an operator may view the operative site through a microscope 601 with a stereoscopic foldable tube, such as the Carl Zeiss F170 Foldable Tube, which allows for magnification, flexibility and operator comfort. The microscope may be integrated with a reflecting prism 602 that redirects the OCT IR signal 603 from a laterally mounted OCT scanner/receiver (not shown) that may be manipulated to redirect the OCT signal 603 off the prism 602 into different portions of the eye. In this embodiment, the visual light paths 604 and 605 are spaced to avoid interference with the OCT signal 603 when they pass through the shared lens stack 606. In this way, the visual light microscopy paths may be unaffected by the OCT signal paths, allowing for the optical assembly to be integrated for a smaller footprint in the operating room. Using the integrated optical assembly, the operator may manually position and aim the optical assembly over the eye.

Figure 7:
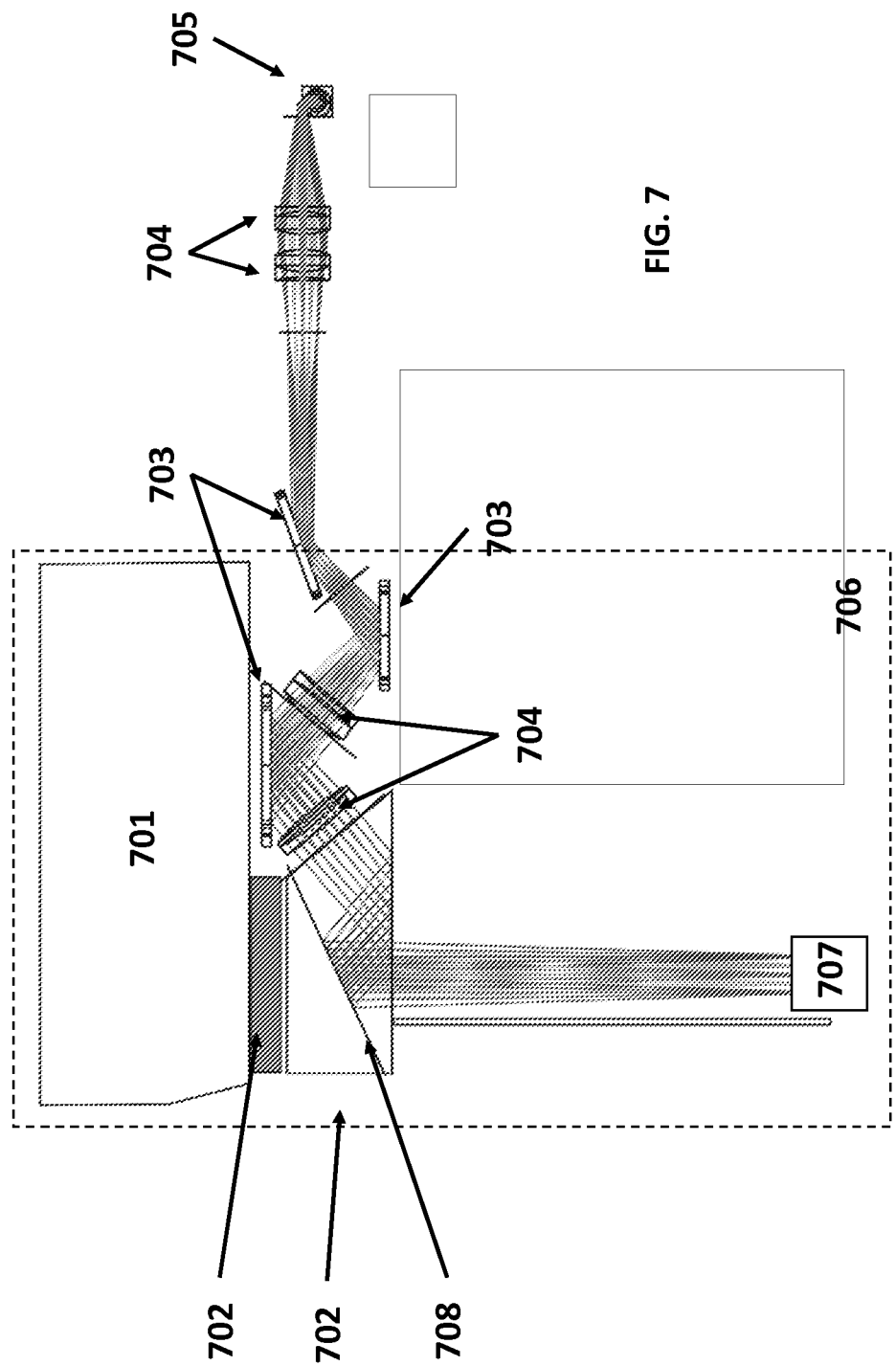
FIG. 7 illustrates an optical apparatus that uses shared optics for both a visual light microscope and an OCT system, in accordance with an embodiment of the present invention.

FIG. 7 illustrates an optical apparatus that uses shared optics for both a visual light microscope and an OCT system, in accordance with an embodiment of the present invention. System 700 broadly comprises a visual light microscope 701, a combining prism assembly 702, and a series of infrared mirrors 703, a series of infrared achromatic lenses 704, and an OCT emitter and detector unit 705. In system 700, the OCT unit 705 both emits and detects OCT signals that are subsequently focused and directed through a combination of both infrared achromatic lens 704 and infrared mirrors 703 to the optical assembly 706 which houses the microscope 701, the combining prism 702, and the output lens 707. Manipulation of the achromatic lens 704 and infrared mirrors 703 allows the system 700 to direct the OCT signal to different portions of the combining prism 702 when attempting to scan different portions of the operative region. For example, infrared mirrors 703 may be rotated to direct the OCT signal off a different portion of combining prism 702. The resulting reflected signal would be directed at a different part of the eye.

Within the optical assembly 706, the visual light optics in microscope 701 are aligned through the objective lens mount 706 into the combining prism assembly 702. The combining prism assembly 702 comprises two separate pieces, separated by a glued dielectric coating at the interface 708. The coating provides a highly reflective surface to infrared light, ensuring that the OCT signal is directed towards the output lens 707, which is situated above the patient's eye (not shown). Conversely, the coating also allows visual light to pass through the combining prism undisturbed, rendering the combining prism highly transmissible to visible light. Thus, using system 700, an operator may visually view the operative site through the microscope 701 to position the optical assembly 706 while also directing the OCT signals onto the operative site using the same assembly.

In some embodiments, one or more downward facing lasers positioned on the exterior of the optical assembly may be used to "aim" the optical assembly over the eye.

In step 504, the system 400 may focus and align the operative region on the eye. In some embodiments, alignment and focus may be performed manually, using the means of aiming and positioning discussed with respect to step 503. In some embodiments, this may be performed robotically. For example, in some embodiments, the system 400 may use an infrared sensor and aiming lasers to align the optical assembly 402. In other embodiments, system 400 may use a visual light camera sensor to autofocus on the operative region.

In step 505, the system 400 may then calculate the location of the operative region (e.g., eye cornea, sclera) using the global coordinate system and the focal length of the optical assembly 402. The system 400 may extrapolate the location of the operative region based on the location of the arm 401, the tip of the optical assembly 402, and the straight-line focal length of the OCT system. Interpolating the location data, the global coordinate system may register three-dimensional coordinates to each of the main components, e.g., arm 401, optical assembly 402, including the operative site 409.

In step 506 of FIG. 5B, the OCT camera may scan the operative region by maneuvering the galvanometer-linked reflector. As discussed with respect to the embodiments in FIGS. 4, 6, and 7, as the galvanometer in reflecting unit 412 directs laser light across the operative region, scattered and reflected laser light will be simultaneously reflected back through the lens stack back to the reflecting unit 412. In turn, the reflector will direct the scattered and directed laser light towards the laser detector 403, often conveyed through an optical fiber 413. Because the OCT data is retrieved by scattering from focused laser light directed at a specific portion of the operative region, the returned OCT data may be represented as image slices or segments of the eye, each showing a specific cross-section. The contours in the image are generated by transitions in the indices of refraction caused by different anatomical features; thus, presenting an anatomical cross-section.

Figure 8:
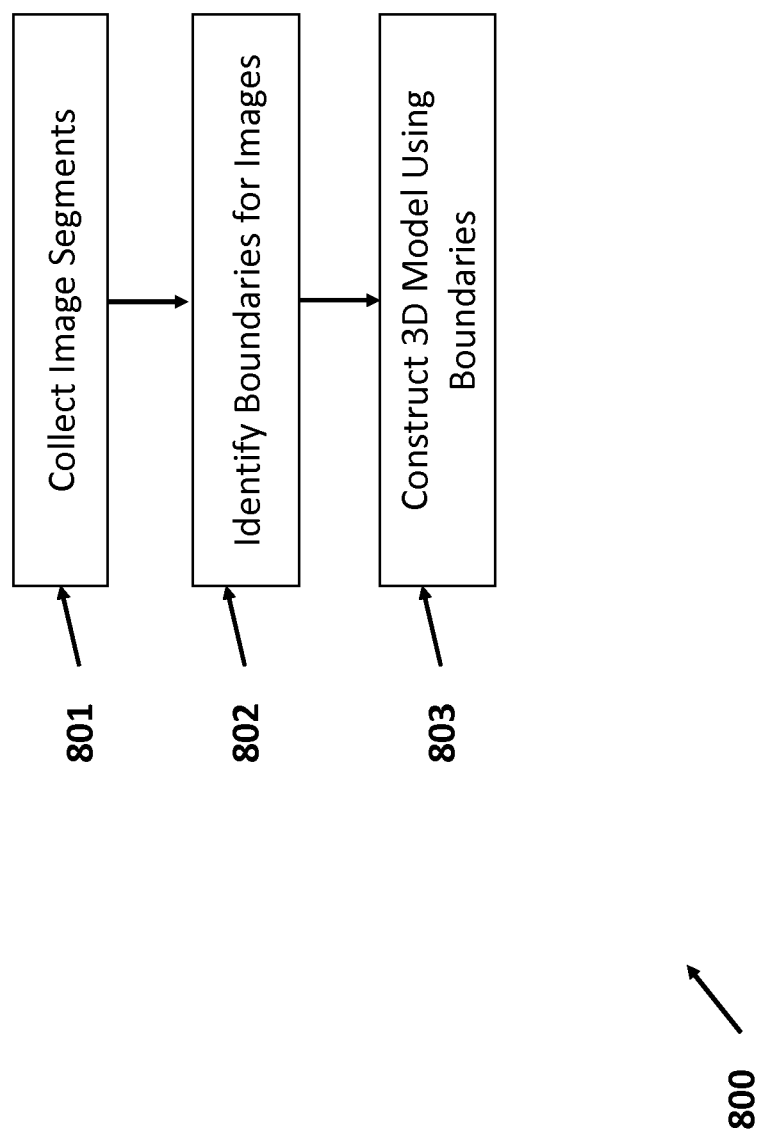
FIG. 8 illustrates a flow diagram that shows how the system may generate a three-dimensional model of the optical region based on OCT data received in image segments, in accordance with an embodiment of the present invention.
Figure 9:
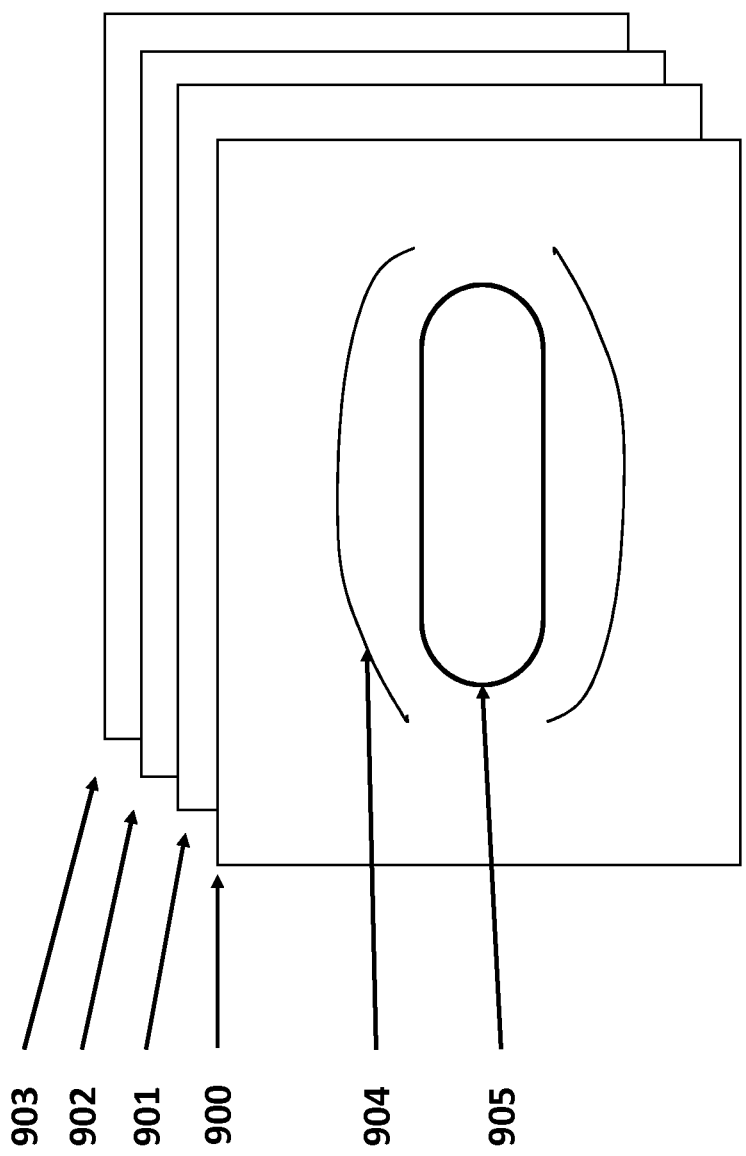
FIG. 9 illustrates a series of OCT image segments from a patient's eye that may be collected by an OCT system, in accordance with an embodiment of the present invention.

In step 507, the processing unit 404 may construct a three-dimensional model of the operative region based on the OCT data received by the optical assembly. FIG. 8 illustrates a flow diagram that shows how the system may generate a three-dimensional model of the optical region based on OCT data. Having generated OCT-based cross-sections, in step 801 from process 800, the image slices and segments may be collected for analysis by processing unit 404. FIG. 9 illustrates a series of OCT data slices from an eye that may be collected by the system, in accordance with an embodiment of the present invention. An OCT scan typically generates series of cross-section scans, which may be visualized as slices 900, 901, 902, and 903 in FIG. 9.

Having collected image segments/slices of the operative region, i.e., the eye, in step 802 of process 800, the system may then analyze the images for anatomical contours and boundaries. For example, in image 900 from FIG. 9, the processing unit 404 may resolve line 904 to represent the sclera of the patient's eye and resolve lines 905 as the outline of the lens capsule. Each contour may then be mapped in x- and y- coordinates of Cartesian space. The system may repeat this identification process for all of the OCT image segments.

Having identified recognizable anatomical contours and landmarks, in step 803 of process 800, the processing unit 404 may combine the mappings of the anatomical contours and landmarks in x- and y- space from the separate image segments to generate a three-dimensional model of the anatomical contours in three-dimensional space. Coordinates in the z- space may be derived using the angle of the galvanometer in reflecting unit 412 at the time the OCT image was captured. The angle of the galvanometer in reflecting unit 412 may be used to derive which portion of the eye was scanned at the time the OCT image was captured. Through repeated iterations of analyzing the x- and y- coordinates generated in step 802 with the angle of the galvanometer, extrapolations into the z-coordinate space may be derived, allowing the system to generate a three-dimensional model in the x-, y-, and z-coordinate planes.

Returning to FIG. 5B, having generated a three-dimensional model of the eye, in step 508 of process 500, the system may register the model to the global coordinate system that includes the registration of the mechanical arm, optical assembly and arm base. Given the system's knowledge of the kinematics of the arm, the general location of the operative region, and the focal length of the lens stack in the optical assembly, the system may precisely register the model, and thus the interior of the eye, to the larger, global coordinate system.

In some embodiments, the three-dimensional model may overlay through the view of the eye through the visual light microscope to assist with aligning the optical assembly over the eye. In other embodiments, the view of the eye through the visual light microscope may include reticles and aiming targets to assist the user with identifying anatomical landmarks for alignment.

Having registered the eye to the global coordinate system, in step 509 of process 500, the system may establish surgical boundaries to restrict maneuvers by a robotic tool within the confined anatomical space of the eye. In practice, having generated the ocular surface data, which is registered to the global OCT established world coordinate system, and further having tool tip position in the same coordinate system, an artificial safety barrier may be robotically enforced to prevent the robot from breaching a specified minimum distance between the tool and the surface. This barrier may be used to prevent potential unwanted anatomical collisions. In other words, the system may prevent the tool tip from entering an established "keep out" zone. In other embodiments, an audible warning may be sounded to alert the operator (physician) if the instrument tip approaches within a certain distance of the retinal tissue.

Various challenges exist under this boundary establishment modality, namely; shadowing caused by tools, regions of the anatomy obstructed from view and movement of the anatomical target. Tool shadows occur when OCT scanning signals cannot penetrate surfaces that are opaque to its wavelength. Analyzing tool-based shadows may be used to identify the location of the tool relative to the operative site. In some embodiments, to compensate, the system may interpolate topology of the anatomy based on topology of the surfaces near the obscured region. In similar fashion, the same technique can be used to overcome areas obscured from the global OCT system's view, such as the equatorial regions of the capsule.

Figure 10:
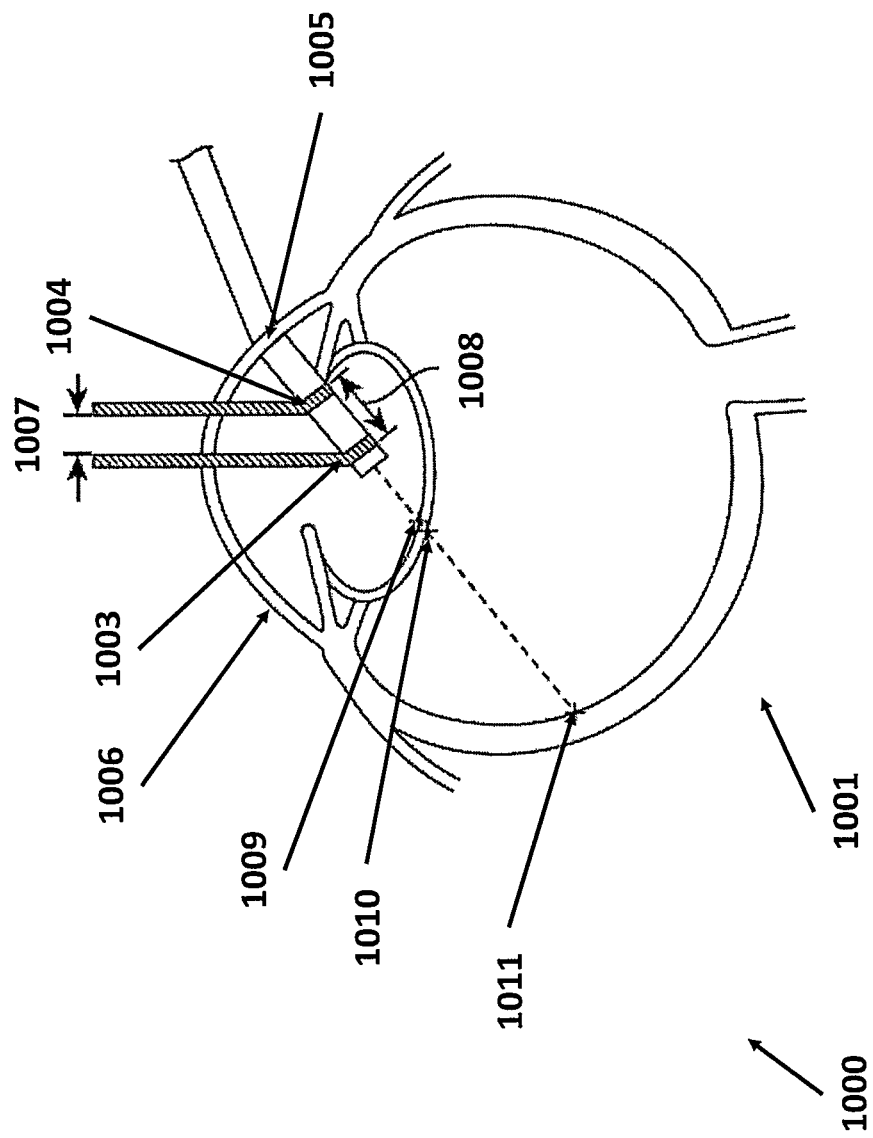
FIG. 10 illustrates the use of a surgical tool with reflective strips that are configured to be registered in an OCT system, in accordance with an embodiment of the present invention.

To facilitate the use of surgical boundaries, certain embodiments make use of surgical tools that may be registered to the global coordinate system using OCT. FIG. 10 illustrates the use of a surgical tool with reflective strips that are configured to be registered in an OCT system, in accordance with an embodiment of the present invention. As shown in diagram 1000, an elongated surgical tool 1002 with reflective markers 1003 and 1004 located along its length may be operated within a patient's eye 1001 through an incision 1005 in the patient's sclera 1006. Real-time determination of tool position using the global OCT system may be achieved through monitoring OCT signal scattering off reflective markers 1003 and 1004 on tool 1002. Reflective markets may be formed using retro-reflective prisms (similar to those found on street signs), reflective coatings or selective polishing.

Retro-reflective markers direct light back towards the OCT detector at the inverse of the incidence vector. This phenomenon results in a strong OCT signal spike, known as an "autocorrelation" signal. Thus, in embodiments where the marker is located at the distal end of the tool 1002, a spike in the OCT signal may be used to identify the tip of the tool 1002.

To prevent the autocorrelation signal from saturating the OCT detector, the tool may use a series of retro-reflective strips, spaced at various distances between them (similar to bar codes), the configuration of which is also specific to instrument type, tip location could be determined through kinematic calculations. Thus, using the (known) shape of the tool, such as the distance between the strips (1007) and the distance of striped area (1008), the system may kinematically determine the position and orientation of the tool 1002 within the eye 1001. Moreover, the measured autocorrelation signals may be compared to the expected locations of the autocorrelation signals, based on the kinematics of tool 1002, to further determine the exact position and vector of the tool 1002.

C. Tool-Based OCT Scanning.

In addition to a global coordinate system, the present invention provides for the use of tool-based OCT scanning to measure for tool position relative to anatomical structures, label imaged structures and monitor for acute changes in anatomy.

In some embodiments, a surgical tool may comprise an embedded optical fiber to emit an OCT scanning signal from the tool tip and an OCT detector to detect the resulting scattering from that radiation. In doing so, the tool may be able to scan and detect structures directly in front of the tool tip. Using the tool registration techniques disclosed earlier, the information received by the OCT detector in the tool may also be incorporated into the global coordinate system.

Returning to tool 1002 in FIG. 10, tool 1002 may be configured with an OCT fiber and coupled to an OCT scanner and detector (not shown). Tool 1002 may scan tissues in eye 1001 by emitting an OCT signal directed to a portion of the lens capsule. Within the eye 1001, the OCT signal may penetrate and scatter IR radiation as it passes through the lens capsule anterior wall 1009, the lens capsule posterior wall 1010, and intersect with the sclera 1011. In some embodiments, the tool-based OCT system may be able to generate A-mode, B-mode, and C-mode OCT scans for analysis.

Figure 11A:
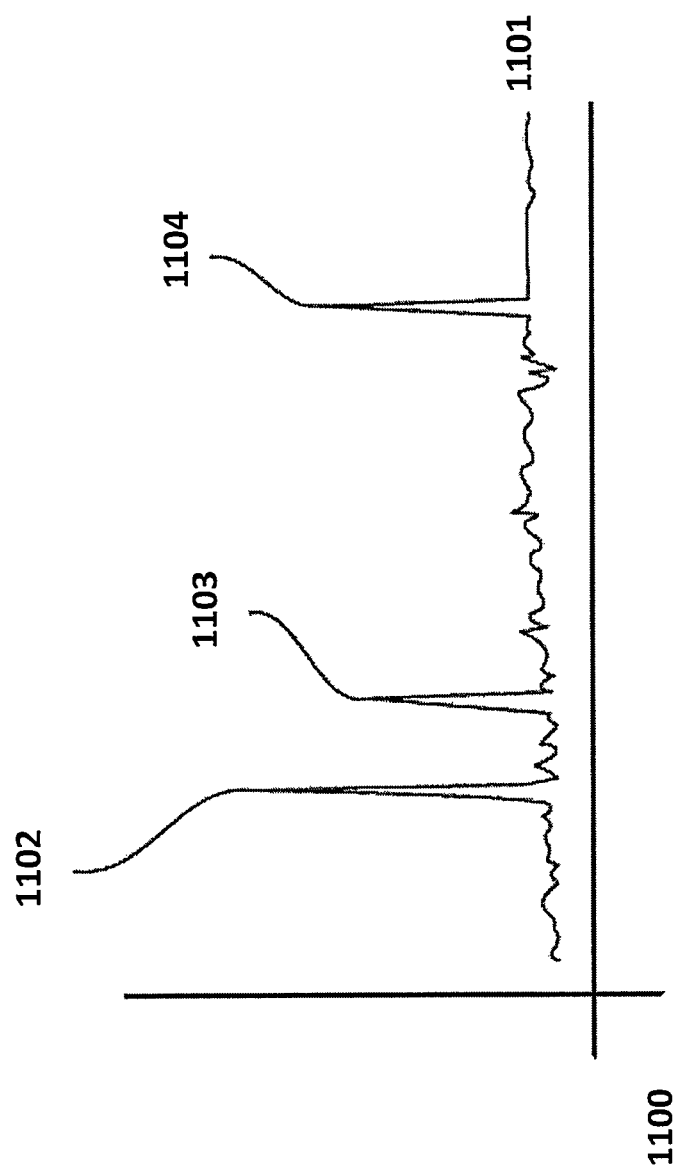
FIG. 11A illustrates a spectrograph showing the expected results of using the tool-based OCT system in tool 1002 from FIG. 10, in accordance with an embodiment of the present invention.

FIG. 11A illustrates a spectrograph showing the expected results of using the tool-based OCT system in tool 1002 from FIG. 10. Spectrograph 1100 represents the spectral intensity of the OCT signal received at the detector. As shown in spectrograph 1100, the signal 1101 scatters at three independent locations at a change of an Index of Refraction, and is detected by the OCT signal detector as a signal "peak" or "spike." As would be recognized by one skilled in the art, the spikes representing signal scattering as the signal passes through a different anatomical boundary. For example, spike 1102 represents the crossing of the lens capsule anterior wall. Spike 1103 represents the crossing of the lens capsule posterior wall into the vitreous. Spike 1104 represents the signal intersection with the solid sclera tissue wall. Thus, system can anticipate what surfaces it should see given this instrument position and correlate the signal spikes with the anatomy expected to be viewed.

Figure 11B:
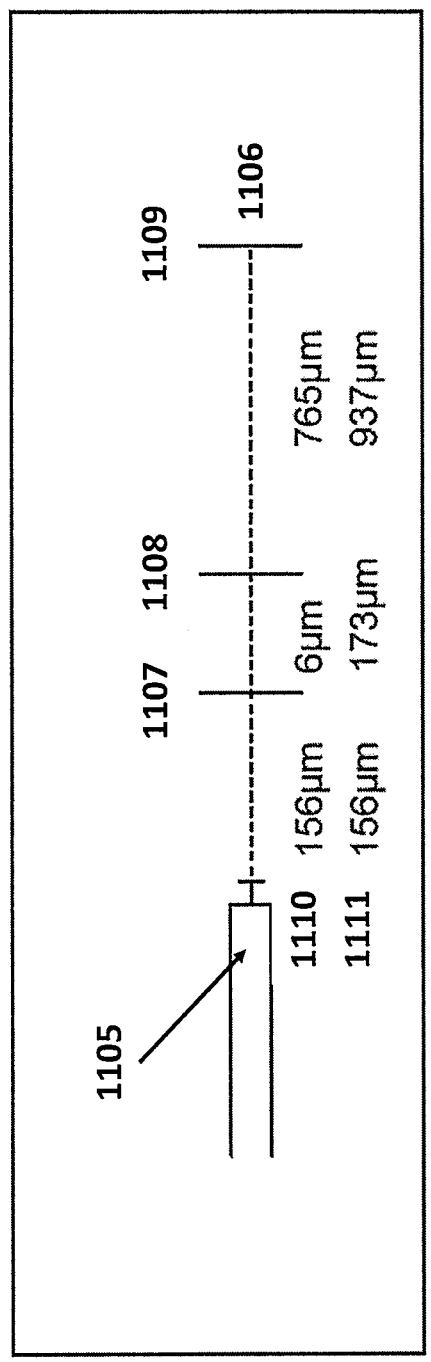
FIG. 11B illustrates how the spectral spikes may be analyzed to determine the relative depth of the anatomical features, in accordance with an embodiment of the present invention.

The resulting spectral data, including the spectral spikes, may be analyzed to determine tissue topology and the relative depth of corresponding anatomical features. FIG. 11B illustrates how the spectral spikes may be analyzed to determine the relative depth of the anatomical features. As shown on the distance chart 1106, spikes 1102, 1103, and 1104 occur at specific distances from the detector 1105 corresponding to distances marked as 1107, 1108, and 1109. These distances may be measured independently between the spikes as shown by row 1110, or as a measure of cumulative distance from the detector as shown by row 1111.

Utilizing the methods for determining tool registration described above, and extrapolating a vector position for the OCT signal, the OCT data may be incorporated into the global coordinate system. In doing so, the tool-based OCT data may be used to provide a more detailed three-dimensional anatomical model than using OCT data from the optical assembly alone. With the tool-based OCT data, the anatomical three-dimensional model labeled with names and thicknesses.

In certain embodiments, the tool-based OCT may monitor tool tip proximity to tissue at a rate of 50 Hz, which allows for monitoring aggressive changes in tissue position relative to robotic manipulation. Thus, if an anatomical change occurs that puts the tool at risk of colliding with either the safety boundary or actual anatomy, the system may withdrawal the tool to a safe position.

Figure 12A:
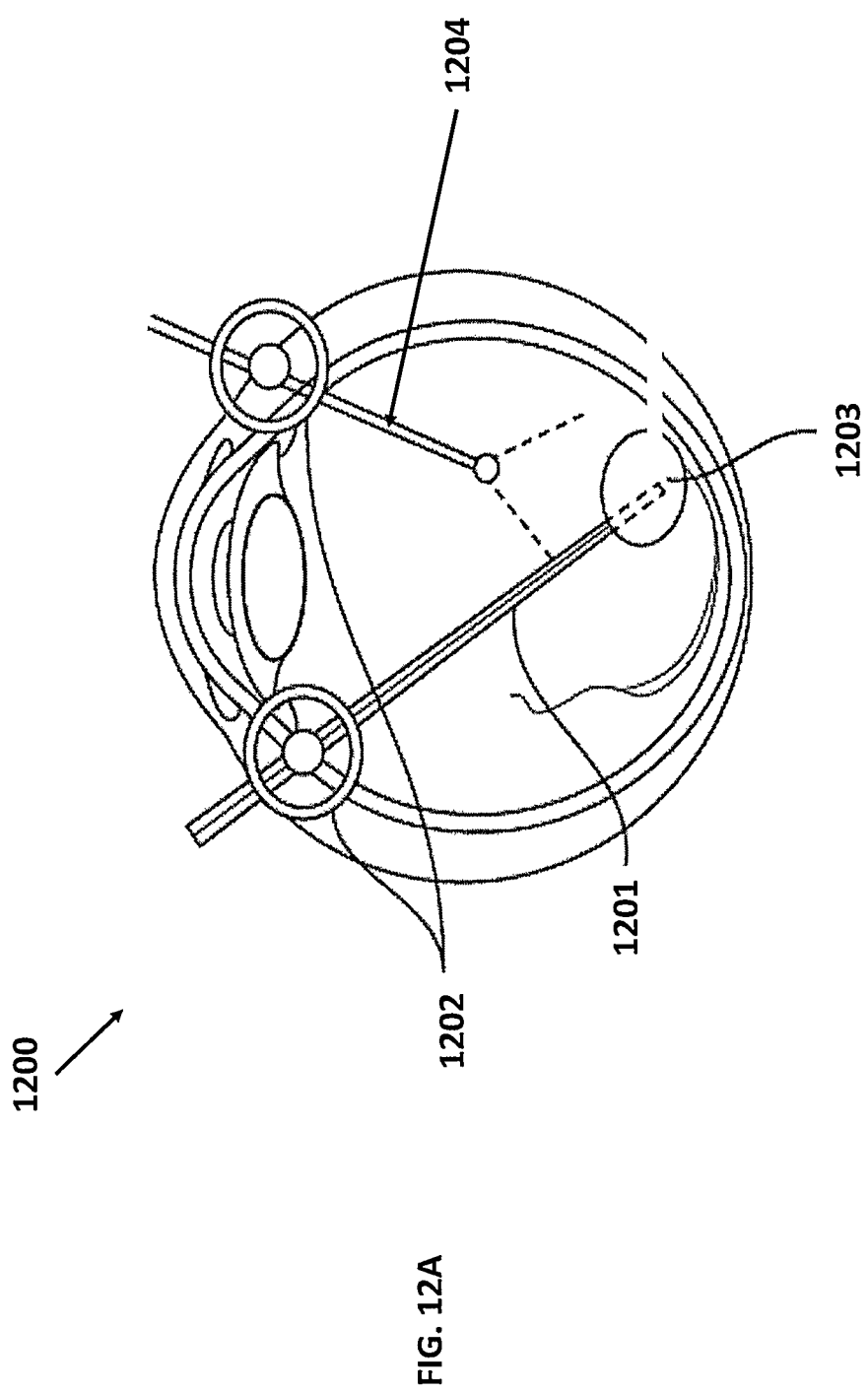
FIGS. 12A and 12B illustrates the use of a global OCT-based coordinate system and related surgical tool for peeling the internal limiting membrane (ILM) during macular surgery, in accordance with an embodiment of the claimed invention.
Figure 12B:
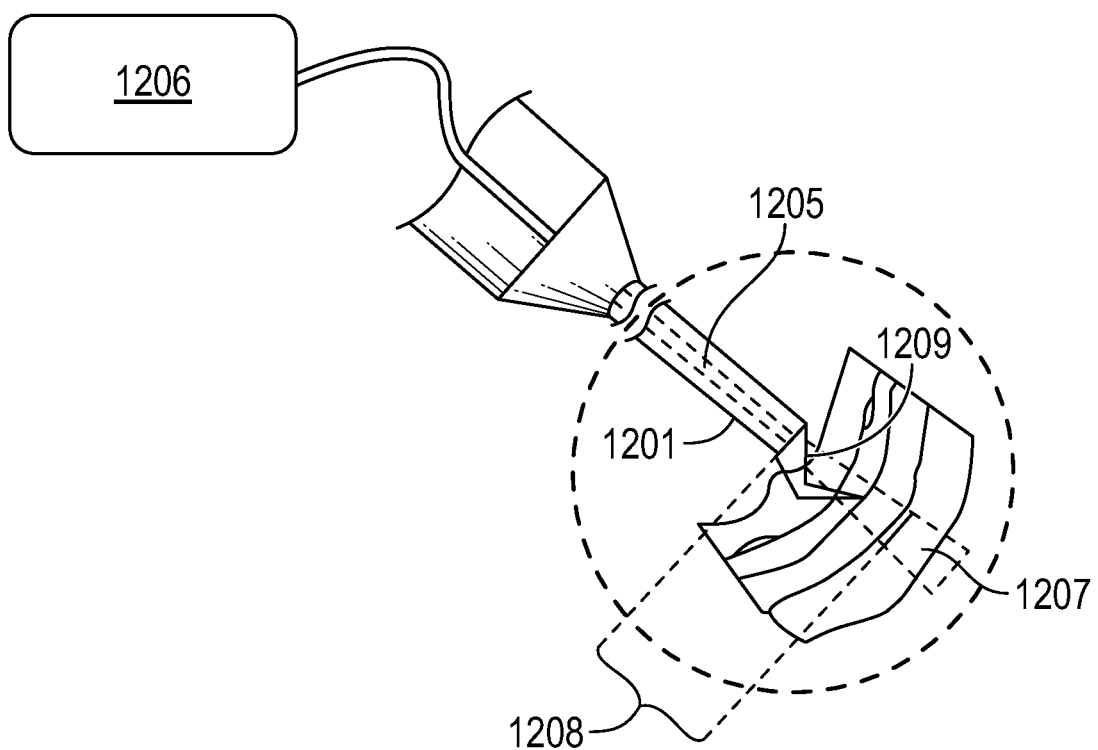

FIGS. 12A and 12B illustrates the use of a global OCT-based coordinate system and related surgical tool for peeling the internal limiting membrane (ILM) during macular surgery, in accordance with an embodiment of the claimed invention. A common issue encountered during retinal surgery is the detection of an edge of the ILM for the surgeon to grasp in order to remove the ILM. The precision of real-time tool-based OCT images may ease that process. Similarly, macular holes and other retinal artifacts may be easily be visualized and identified with this enhanced visualization capability.

FIG. 12A illustrates use of surgical tools in a cutaway view of a patient's eye, in accordance with an embodiment of the present invention. As shown in FIG. 12A, surgical tool 1201 may be inserted into the eye 1200 through insertion points 1202 for access to a location on the retina, i.e., the operating area 1203. In addition, in some embodiments, a second surgical tool 1204 may be inserted into the eye 1200. While the first surgical tool 1201 may include a surgical pick at its distal end, the second surgical tool 1204 may utilize imaging means or illumination means at its distal end in order to enhance the vision of the first surgical tool 1201. Consistent with earlier embodiments, tools 1201 and 1204 may be registered to a global coordinate system using the devices and methods discussed earlier.

FIG. 12B illustrates a schematic drawing with a close up view of surgical tool 1201 at the operating area 1203 from FIG. 12A. Tool 1201 may comprise an OCT fiber 1205 receiving an OCT signal from an OCT system 1206, which may comprise both an OCT emitter and OCT detector. The OCT fiber 1205 may be used to scan the tissue topology with infrared OCT radiation (represented by the area enclosed by dotted lines 1207). Using the results from the OCT scans, an operator (physician) may determine the distance of the tool 1201 from the surface (1208). With the help of the resulting OCT-based tissue topology, the OCT scans may also help identify a candidate edge of the ILM for grasping with a surgical pick 1209, often a very difficult process in particular ophthalmological surgeries.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:

1. A system for facilitating robotic surgery, comprising:
a first mechanical arm configured to facilitate operation of an optical assembly that comprises optical components and an optical detector coupled to the first mechanical arm, the first mechanical arm comprising a first joint sensor configured to generate a first location reading for the first mechanical arm;
a second mechanical arm coupled to a surgical tool, the second mechanical arm comprising a second joint sensor configured to generate a second location reading for the second mechanical arm, the surgical tool comprising an optical fiber configured to emit a scanning signal from a distal end of the surgical tool and receive a signal resulting from scattering of the scanning signal;
a visual light microscope configured to provide a view of a target anatomy, the visual light microscope sharing at least one of the optical components of the optical assembly, the at least one shared optical component configured to provide light in a first frequency range to the visual light microscope and provide light in a second frequency range to the optical detector; and
a processor,
wherein the processor is configured to determine locations of the first and second mechanical arms and the tool based on the first and second location readings,
wherein the processor is configured to generate kinematic registration data for the first and second mechanical arms and the tool based on the determined locations,
wherein the processor is configured to obtain a plurality of image slices of the target anatomy based on a signal output from the optical detector,
wherein the processor is configured to generate imaging data including a three-dimensional data model of the target anatomy based on the image slices and the signal resulting from scattering of the scanning signal received from the optical fiber, the three-dimensional data model comprising anatomical contours defining surface data of the target anatomy,
wherein the processor is configured to generate a global coordinate system using the imaging data and the kinematic registration data,
wherein the first and second mechanical arms are robotically-driven, and
wherein the processor is configured to automatically limit movement of the first and second mechanical arms to robotically enforce a virtual boundary comprising a specified distance between the tool and a surface of the target anatomy utilizing the generated global coordinate system, a position of the target anatomy therewithin, and the surface data for avoiding inadvertent injury to the target anatomy.

2. The system of claim 1, wherein the movement of the first or second mechanical arm into the virtual boundary triggers auditory feedback.

3. The system of claim 1, wherein the optical assembly is configured to generate stereoscopic images of tissue topology.

4. The system of claim 1, wherein the first and second joint sensors comprise torque sensors.

5. The system of claim 4, wherein the first and the second mechanical arms are coupled to one or more movable carts.

6. The system of claim 1, wherein the first joint sensor comprises a first torque sensor coupled to a first linkage of the first mechanical arm.

7. The system of claim 6, wherein the second joint sensor comprises a second torque sensor coupled to a second linkage of the second mechanical arm.

8. The system of claim 1, wherein the first joint sensor comprises a first plurality of joint sensors coupled to a plurality of linkages of the first mechanical arm.

9. The system of claim 1, wherein the second joint sensor comprises a plurality of joint sensors coupled to a plurality of linkages of the second mechanical arm.

10. The system of claim 1, wherein:
the tool comprises reflective markers,
the optical assembly is configured to generate the imaging data based on light reflected from the reflective markers, and
the processor is configured to determine a position of the tool based on the imaging data.

11. The system of claim 10, wherein the reflective markers comprise reflective strips.

12. The system of claim 1, wherein the processor is configured to: determine that an anatomical change has occurred that would put the surgical tool at risk of colliding with the virtual boundary based on the signal resulting from scattering of the scanning signal received from the optical fiber; and withdraw the surgical tool in response to determining that the anatomical change has occurred.

13. A method for facilitating robotic surgery using a global coordinate system, the method comprising:
determining the location of a first robotically-operated mechanical arm with a first joint sensor on the first robotically-operated mechanical arm;
registering the determined location of the first robotically-operated mechanical arm to a global coordinate system with a processor;
registering the location of an optical assembly with a predetermined focal length to the global coordinate system with the processor, the optical assembly comprising optical components and an optical detector and being operatively coupled to the first robotically-operated mechanical arm;
determining the location of a second robotically-operated mechanical arm with a second joint sensor on the second robotically-operated mechanical arm, the second mechanical arm coupled to a surgical tool comprising an optical fiber;

registering the determined location of the second robotically-operated mechanical arm to the global coordinate system with the processor;

utilizing a visual light microscope configured to view a target anatomy, the visual light microscope sharing at least one of the optical components of the optical assembly, the at least one shared optical component configured to provide light in a first frequency range to the visual light microscope and provide light in a second frequency range to the optical detector;

orienting the optical assembly relative to an operative site in which the target anatomy is located;

registering the location of the operative site in the global coordinate system with the processor using the predetermined focal length of the optical assembly;

scanning the operative site using an optical system integrated into the optical assembly;

retrieving optical data with the processor, the optical data comprising a plurality of image slices of the operative site including the target anatomy based on a signal output from the optical assembly;

emitting a scanning signal from the optical fiber at a distal end of the surgical tool;

receiving a signal at the optical fiber resulting from scattering of the scanning signal;

processing the image slices and the signal resulting from scattering of the scanning signal received from the optical fiber with the processor to generate a three-dimensional model of the operative site and the target anatomy, the three-dimensional data model comprising anatomical contours defining surface data of the target anatomy;

registering the three-dimensional model to the global coordinate system with the processor; and automatically limiting movement of the second robotically-operated mechanical arms to robotically enforce a virtual boundary in the global coordinate system with the processor, the virtual boundary comprising a specified distance between the surgical tool and a surface of the target anatomy utilizing the registered three-dimensional model of the operative site in the global coordinate system and the surface data.

14. The method of claim 13, further comprising:

determining that an anatomical change has occurred that would put the surgical tool at risk of colliding with the virtual boundary based on the signal resulting from scattering of the scanning signal received from the optical fiber; and withdrawing the surgical tool in response to determining that the anatomical change has occurred.

* * * * *